US006358534B1

(12) United States Patent
Schwarz et al.

(10) Patent No.: US 6,358,534 B1
(45) Date of Patent: Mar. 19, 2002

(54) IMMUNOTOLERANT PROTHROMBIN COMPLEX PREPARATION

(75) Inventors: Hans-Peter Schwarz, Vienna; Peter Turecek, Klosterneuburg, both of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/402,582

(22) PCT Filed: Apr. 6, 1998

(86) PCT No.: PCT/AT98/00091

§ 371 Date: Jan. 28, 2000

§ 102(e) Date: Jan. 28, 2000

(87) PCT Pub. No.: WO98/44942

PCT Pub. Date: Oct. 15, 1998

(30) Foreign Application Priority Data

Apr. 8, 1997 (AT) .............................................. A 594/97
Sep. 19, 1997 (AT) ........................................... A 1592/97

(51) Int. Cl.⁷ .............................................. A61K 35/16
(52) U.S. Cl. ...................... 424/529; 424/530; 424/94.2; 435/2; 435/3
(58) Field of Search ................................ 424/94.2, 529, 424/530; 435/2, 3

(56) References Cited

U.S. PATENT DOCUMENTS 4,286,056 A * 8/1981 Andary et al. ................. 435/3
5,186,945 A   2/1993 Shanbrom

FOREIGN PATENT DOCUMENTS

| CA | 2185859 | 3/1997 |
|---|---|---|
| EP | 0 044 343 A1 | 1/1982 |
| EP | 0 082 182 B1 | 6/1983 |
| EP | 0 083 999 A1 | 7/1983 |
| EP | 0 131 740 A2 | 1/1985 |
| EP | 0 197 554 B1 | 10/1986 |
| EP | 0 479 597 A2 | 4/1992 |
| EP | 0 764 447 A2 | 3/1997 |
| EP | 0 765 669 A1 | 4/1997 |
| GB | 2 080 312 A | 2/1982 |
| WO | WO 81/02105 | 8/1981 |
| WO | WO 83/00016 | 1/1983 |
| WO | WO 93/14791 | 8/1993 |
| WO | WO 96/35710 | 11/1996 |

OTHER PUBLICATIONS

Hornsey et al., J Clin Pathol 41: 562–567 (1988).*
International Search Report for PCT/AT98/00091, dated Jul. 15, 1998.
Ames, B.N., "Assay of Inorganic Phosphate, Total Phosphate and Phosphatases" *Methods in Enzymology*, vol. 8, 1966, pp. 115–118.
Auperin, D.D. et al., "Studies on the Virucidal Properties of Amphipathetic Substances" *Chem. Ab.*, vol. 9, 1981, Abstract # 95:73325f.

Blumi, G. et al., "Protein Free Culture of R–CHO and Hybridoma Cells on the Macroporous PolyporE® Carrier", *Chem. Ab.*, vol. 9, 1981, Abstract # 95:73325f.
Fischer, B. et al., "Structural Analysis of Recombinant von Willebrand Factor: Identification of Hetero– and Homo–dimers", *FEBS Letters*, vol. 351, 1994, pp. 345–348.
Guerrier L. et al., Chromatographic Supports Used to Remove Solvent–Detergent Mixtures Used as Virus–Inactivating Agents, *Chem. Abs.*, vol. 125, 1996 p. 21, Abstract # 48242g.
Hedner, U. et al., "Clinical Experience with Human Plasma–Derived Factor VIIa in Patients with Hemophilia A and High Titer Inhibitors", *Haemostasis*, vol. 19, 1989, pp. 335–343.
Mariani, G. et al., "Contact Activation and Factor VII After the Use of an Activated Prothrombin Complex Concentrate (FEIBAR) in Hemophiliacs with Inhibitors", *Thrombosis Res.*, vol. 31, 1983, pp. 475–488.
Myers, R. et al., "Large–Scale Preparation of a Highly Purified Solvent–Detergent Treated Factor VIII Concentrate", *Pharm.*, vol. 115, 1991, p. 401, Abstract # 35559j.
Moritz, B et al., "Immunozym F VIII:Ag, a Novel Assay for the Determination of F VIIO Antigen", *Thrombosis and Haemostasis*, 1997, p. 31, Abstract #PS–122.
Oxford, John S. et al., "Inactivation of Influenza and Other Viruses by a Mixture of Virucidal Compounds", *Mic. Biochem.*, vol. 75, 1971, p. 147, Abstract # 1752g.
Piet, M.P.J. et al., "the Use of Tri(n–butyl)phosphate Detergent Mixtures to Inactivate Hepatitis Viruses and Human Immunodeficiency Virus in Plasma and Plasma's Subsequent Fractionates" *Chem. Abs.*, vol. 114, 1991, p. 3941, Abstract # 39082a.
Prince, A.M. et al., "Inactivation of Hepatitis B and Non–A, Non–B Viruses by Combined Use of Tween 80, β–propiolactone, and Ultraviolet Irradiation", *Pharm.*, vol. 99, 1983, p. 381, Abstract # 218552x.
Schlokat, U. et al., "large Scale Production of Recombinant von Willebrand Factor", *Thrombosis and Haemostasis*, vol. 78, 1995, p. 1160, Abstract # 993.
Strancar, A. et al., "Extraction of Triton X–100 and its Determination in Virus–Inactivated Human Plasma by the Solvent–Detergent Method", *Pharm.*, vol. 120, 1994, p. 653, Abstract # 173177n.
Teitel, J.M., "The Factor VIII Bypassing Activity of Prothrombin Complex Concentrates: The Roles of Factor VIIa and of Endothelial Cell Tissue Factor", *Thrombosis and Haemostasis*, vol. 66, 1991, pp. 559–664.

(List continued on next page.)

Primary Examiner—Jean C. Witz
(74) Attorney, Agent, or Firm—Oppenheimer Wolff & Donnelly LLP

(57) ABSTRACT

The invention relates to an immunotolerant prothrombin complex preparation, a method of producing this preparation, as well as the use of the preparation for producing a medicament,

60 Claims, No Drawings

OTHER PUBLICATIONS

Turecek, P.L. et al., "Thrombogenicity of Recombinant Factor VIIa and Recombinant Soluble Tissue Factor in an in vivo Rabbit Model", *Thrombosis and Haemostasis*, 1997, p. 222, Abstract # PS–903.

van den Ouweland, A.M.W. et al., "Structural Homology Between the Human fur Gene Product and the Subtilisin–like Protease Encoded by Yest KEX2", *Nuc. Acids Res.*, vol. 18, 1990, p. 664.

Vinazzer, H., "Comparison Between Two Concentrates with Factor VIII Inhibitor Bypassing Activity", *Thromb. Res.*, vol. 26, 1982, pp. 21–29.

Ad Hoc Working Party on Biotechnology/Pharmacy Note for Guidance, "Validation of Virus Removal and Inactivation Procedures", Commission of the European Communities, pp. 1–15.

The Journal of Biological Chemistry, "A Simple Method for the Isolation and Purification of Total Lipides From Animal Tissues", McLean Hospital Research Laboratories, Waverley, and the Department of Biological Chemistry, Harvard Medical School, Boston, Massachusetts, Commission of the European Communities, 1956, pp. 497–509.

* cited by examiner

IMMUNOTOLERANT PROTHROMBIN COMPLEX PREPARATION

The invention relates to a pharmaceutical composition for treating blood coagulation disorders, in particular for treating factor VIII inhibitor patients. The invention furthermore relates to a method for preparing such a composition as well as the use thereof.

Blood coagulation is triggered by a series of consecutive reactions of different proteins and enzymes, respectively. By a deficiency of blood coagulation factors, the formation of fibrin from fibrinogen and, thus, wound closure, is prohibited; the consequence are hemorrhages. Such is the case with hemophilia A. This is the most wide-spread bleeding disease and is caused by a deficiency of factor VIII. For a substitution treatment of hemophilia A, preparations are used which contain factor VIII. Treatment with these preparations in most instances leads to a rapid hemostasis.

There are, however, also patients who do not only suffer from a factor VIII deficiency, but who have also developed an inhibitor directed against factor VIII. A further collective of patients has factor VIII inhibitors without suffering from hemophilia A Depending on the amount of factor VIII inhibitors present, the effect of factor VIII supplied is inhibited by neutralization of the latter.

At present, preparations on the basis of a plasma fraction which contains a mixture of coagulation factors are offered for a treatment of factor VIII inhibitor patients. This plasma fraction may, e.g., comprise the factors of the prothrombin complex (factors II, VII, IX and X). A blood coagulation-promoting preparation having factor VIII inhibitor bypass activity (FEIBA® TIM 4, from BAXTER AG) is, e.g., obtained according to AT-B 0 368 883 by treating cryosupernatant. This preparation also comprises the coagulation factors II, VII, IX and X.

The action of a FEIBA preparation is manifold due to its complex composition. Mariani et al. (Thrombosis Res. 31, 475–488 (1983)) mentions factor VII in its activated form as an active principle. It has been found that after infusion of a FEIBA preparation there occurs an increased content of factor VIIa in the plasma of hemophiliacs.

Likewise, Teitel (Thrombosis and Haemostasis 66 (5) 559–564 (1991)) discusses the role of factor VIIa in prothrombin complex concentrates with a factor VIII bypassing activity. At the same time also the active principle of factor Xa in such preparations is discussed. The prothrombin complex concentrates assayed contained factor VIIa, expressed by the ratio of factor VII activity to factor VII antigen, of 2.1 and 2.5.

The prothrombin-containing therapeutic composition prepared according to EP 0 044 343-B1 is suitable for the treatment of coagulation factor inhibitors and comprises an activated prothrombin complex in which the factors partially are activated The content of factor VIIa is from 8–80 units/ml The factor IX concentration ranges from 15 to 112 units/ml. Accordingly, the content of factor VIIa, based on factor IX, is 0.07–5.3 U of factor VIIa/U of factor IX. Vinazzer (Thromb. Res. 26:21–29 (1982)) shows the difference of the preparations AUTOPLEX, prepared according to EP 0 044 343, and FEIBA. As shown there, AUTOPLEX is characterized by the higher content of thrombin (factor IIa), measured in NIH units, as compared to FEIBA (cf. table 1, page 24).

Yet also highly purified factor VIIa preparations have been suggested for the therapy of coagulation inhibitor conditions (e.g. EP 0 082 182-B1) and Hedner et al. (Haemostasis 19, 335–343 (1989)).

An advantage of factor VIIa preparations is their freedom from factor VIII. The content of factor VIII in prothrombin complex preparations or in activated prothrombin complex preparations such as, e.g., FEIBA, has the effect in patients with functional factor VIII inhibitors that these inhibiting antibodies are boosted by a renewed administration of factor VIII with the consequence that the condition of the inhibitor hemophilia even deteriorates temporarily.

It has, however, been found that for an effective hemostasis in factor VIII inhibitor hemophilia, the action of factor VIIa preparations is interior to that of prothrombin complex factor preparations (Turecek P. et al., Thrombosis & Haemostasis, 1997, p.222).

It is thus an object of the present invention to provide a preparation which has the effectiveness or efficiency of prothrombin complex factor preparations, without, however, leading to the undesired immunological side reactions of such preparations.

The afore-mentioned object is achieved in that according to the present invention, an immunotolerant pharmaceutical prothrombin complex preparation comprising factors II, IX, X and, optionally, VII with a low factor VIII antigen content is provided.

The factor VIII antigen content of the preparation according to the invention preferably is less than 10%, in particular less than 5%. The factor VIII content preferably is less than 0.1 factor VIII:C antigen/U FEIBA. In a particularly preferred embodiment, the factor VIII antigen content is even below 0.03/U FEIBA, more preferred below 0.02/U FEIBA, and most preferred below the detection limit.

The finding that particularly in case of a further purification of the prothrombin complex factors from plasma or from a plasma fraction, the factor VIII content and, optionally, also the phospholipid content can be reduced so much while the activity of the prothrombin complex factors is largely retained must be considered to be surprising.

In particular, the pharmaceutical preparation according to the invention contains at least the factors IXa, Xa and VIIa and has FEIB activity, i.e. it shortens the coagulation time of a factor VIII-deficient plasma with a functional inhibitor (in this context, cf., e.g., AT-B 350 726).

The preparation according to the invention can be prepared from plasma or from a plasma fraction. The plasma fraction may be prepared from plasma, in particular plasma of human origin, by a chromatographic treatment, precipitation or centrifugation, or the supernatant of the cryoprecipitate is used.

The plasma fraction comprises vitamin K-dependent factors, such as factors of the prothrombin complex, yet also proteins S, C and/or Z are preferably contained therein.

In a particularly preferred embodiment, the preparation is free from phospholipids. Preferably, the upper limit of phospholipids contained is 0.1 nmol/U of FEIBA (for a determination, cf. the Examples).

Because of this freedom from phospholipids, the formation of undesired antibodies to factor VIII can be reduced or prevented, respectively.

According to the present invention, also a method or producing this preparation is provided. This method comprises the following steps:

a) Providing plasma or a plasma fraction comprising factors II, IX, X and, optionally, factor VII, b) contacting the plasma or the plasma traction with a carrier material, optionally in the presence of a detergent, so that factor VIII and, optionally, phospholipids are separated from factors II, IX, X and, optionally, factor VII, c) purifying the plasma or the plasma fraction, and d) recovering a fraction comprising factors II, IX, X and, optionally, factor VII.

In a preferred variant, steps b and c or b, c and d, respectively, are carried out as one method step.

The plasma fraction used preferably is one having at least an intermediary purity.

By a "preparation having an intermediary purity", a plasma fraction is to be understood which is analogous to the definition of the intermediary purity of factor VIII preparations (in this context, cf., e.g., Wood Clive (ed.) Factor VIII: Purity and prophylaxis, Royal Society of Medicine).

Accompanying proteins which are not removed by a chromatographic purification thus may still be present in a preparation of intermediary purity.

As the Starting material, a conventional commercially available prothrombin complex factor preparation may be used, such as, e.g., FEIBA S-TIM 4, from BAXTER, or activated prothrombin complex.

As respective purification treatments, the methods known from the prior art are employed, preferably a chromatographic treatment, precipitation or centrifugation is carried out. As plasma fraction, also cryoprecipitate supernatant can be used.

The carrier material is a material suitable for chromatography, filtration and/or nanofiltration. The filtration in particular is an affinity or membrane filtration.

If a pre-purified material is used, e.g. a material pre-purified by means of an anion exchanger, a readsorption on a further carrier material, preferably on the same carrier material as has been used for the pre-purification, is used, under altered conditions.

In a preferred embodiment, the carrier material is a factor VIII-specific carrier material, in particular a matrix suitable for affinity chromatography. Particularly peferably a vWF-containing matrix is used.

To such a carrier material, factor VIII and, optionally, phospholipid are preferably adsorbed, while the factors II, IX, X and, optionally VII, are not bound.

The carrier material may, however, also be a carrier material non-specific for factor VIII, e.g. a weak anion exchanger, e.g. a DEAE, TMAE anion exchanger or further anion exchangers sufficiently known from the prior art.

Depending on the conditions chosen, either factor VIII and, optionally, phospholipids are adsorbed on the carrier material, while factors II, IX, X and, optionally, factor VII are riot bound, or vice-versa.

In a further preferred embodiment, the carrier material has a higher affinity for the prothrombin complex than for factor VIII. Thus, e.g., factors II, IX, X and, optionally, factor VII are adsorbed, while factor VIII and, optionally, phospholipids are eluted Factor VIII may also be specifically inactivated and then may in such inactivated form, e.g., no longer bind to the carrier material. Such an inactivation of factor VIII may, e.g., be effected by dissociation by using e.g. a chelating agent, by degradation, in particular proteolytic degradation, e.g. by means of serine proteases, such as thrombin or activated protein C, by the binding of affinity partners, such as antibodies or peptides.

All the method variants disclosed may also be carried out in the presence of a detergent, in particular of a non-ionic detergent. Preferably, a polyether or a polysorbate is used as the detergent, in particular Tween or Triton is used.

If a detergent is present, in a preferred embodiment it is removed again or separated, respectively.

In a further preferred embodiment, a step of inactivation of possibly present pathogens, in particular selected from the group of heat treatment, vapor treatment, treatment with a solvent and/or treatment with a detergent, is provided.

The preparation according to the invention thus is generally obtainable according to a method described before. It is particularly suitable for producing a medicament which is suitable for the treatment of factor VIII inhibitor (=hemophilia A) patients, in particular for such patients who have an inhibitor titer of greater than 1 Bethesda U/ml plasma, preferably greater than 5 Bethesda U/ml plasma. It may also be produced by a combination of the highly purified individual factors II, IX and X as well as, optionally, factor VII.

Since a biological material, i.e. material derived from organisms or body liquids or microorganisms, may be contaminated with pathogens, such as, e.g., infectious molecules or microorganisms and viruses or pyrogens, respectively, various methods or inactivating or depleting, respectively, pathogens or pyrogens, respectively, have been developed.

Such methods include physical and/or chemical treatments, such as, e.g., diverse filtration methods (e.g. nano-, dia- or ultrafiltration), a heat treatment, treatment with an acid or a base, treatment with a detergent and/or an organic solvent, as well as treatment with OV light or with laser light. Also various combinations of such methods for the inactivation or depletion, respectively, of pathogens have often been suggested in the prior art.

From EP 0 197 554, e.g., a method for depyrogenizing and inactivating viruses in a biological or pharmaceutical product is known which comprises a treatment with a virus-inactivating and depyrogenizing agent, such as, e.g., an amphiphilic substance and/or a solvent, on a solid phase on which the product has been adsorbed. Following this treatment, the virus-inactivating and depyrogenizing agent is separated from the solid phase, the adsorbed product is washed and finally is eluted from the solid phase.

From EP 0 131 740, the treatment of a protein-containing composition in a solution with organic solvents, such as di- or tri-alkyl phosphates, optionally in the presence of a detergent (solvent/detergent treatment) is known, whereby protein compositions free from lipid-containing viruses can he obtained.

From AT patent 402,151, a heat treatment is known in which, prior to heating, a tenside at a concentration of at least 1% by weight is admixed to a preparation which is present in an aqueous solution.

A further method for reducing or suppressing, respectively, undesired activities in biological or pharmaceutical products is known from BP 0 083 999. This method is based on an extended contact with a solution or suspension of a non-denaturing amphiphilic agent. The depyrogenized product is treated with an ion exchanger to remove the amphiphilic agent.

A disadvantage of many of these methods known from the prior art is the frequent occurrence of losses of activity of the labile proteins, e.g. blood proteins, contained in the compositions to be treated. In particular when carrying out a chromatographic purification step, an inactivation of proteins occurs to a relatively high extent. A degradation of proteins may also lead to an activation. Thus, e.g., it is known that during a chromatographic purification, due to autokatalytic processes, factor VII is very easily activated to factor VIIa which is undesired because it is very labile.

A further disadvantage resides in great amount of time and apparatus required for many methods which greatly reduces their practicability and therefore frequently renders them unsuitable for application on a large scale.

Within the scope of the present invention, therefore, a method for effectively inactivating pathogens in biological materials, which is gentle on proteins, in particular on labile proteins, is to be used which can easily be adapted to a large scale and which can he carried out economically. In particular, a degradation and a possible activation of proteins susceptible therefor should largely be avoided in this method for inactivating pathogens.

In this method for inactivating pathogens, in particular viruses, in a biological material this material is incubated with a chemical agent, wherein the incubation is carried out in the presence of an eluotropic salt corresponding to a NaCl concentration of at least 200 mmol/l, preferably at least 300 mmol/l.

Inactivation of pathogens in solution offers some advantageous over the treatment of an adsorbent. Thus, e.g., the practicability of such a method is higher in a homogenous, single-phase system, and validation of the inactivation step is better possible. Moreover, the better accessibility of pathogens in a relatively homogenous phase seems to increase the efficiency of the method step.

The biological material preferably comprises a human protein and, in particular, it is plasma or a plasma fraction or it is derived from a cell culture. Preferably, the biological material comprises a blood factor, such as factors XII, XI, VIII, V, von Willebrand factor or fibrinogen, in particular a vitamin-K-dependent protein, such as factor II, factor VII, factor IX, factor X, protein C, protein S or protein Z, respectively.

The proteins may be present as single factors, preferably in purified form, or in a complex mixture. In a particularly preferred embodiment, the biological material comprises at least one factor of the prothrombin complex and is particularly a prothrombin-complex-containing traction or a factor VII-containing material, e.g. after a cryoprecipitation of plasma, one starts from the respective supernatant (cryosupernatant) thereof.

The preparation according to the invention preferably is one having FEIB activity (Factor Eight Inhibitor Bypassing Activity), i.e. a preparation which is suitable for treating factor VIII inhibitor patients.

The cell culture-derived material preferably is a material comprising recombinantly produced blood factors, among them factors of intrinsic or extrinsic coagulation, of fibrinolysis, of thrombolysis, or the inhibitors thereof, in particular vitamin K-dependent blood factors. As cells, the cells commonly employed for the expression of recombinant proteins can be used, preferably mammalian cells, such as, e.g., Vero, CHO or BHK cells. The respective proteins can be subjected to the inventive method for inactivation of possibly present pathogens either directly from the crude cell extract, or it may also be a pre-purified cell fraction.

The chemical agent is, e.g., a detergent (amphiphilic agent, tenside), which preferably is contained in an amount of at least 1%, more preferred more than 5%, most preferred more than 10%, yet, according to the invention also other chemical agents may be employed, in particular such which are already known to have a virucidal, bactericidal or depyrogenizing effect, or mixtures of the most varying chemical agents, respectively.

The choice is, however, limited in that the nativity of the biological material shall not be substantially adversely affected. For an economical mode or procedure, a chemical is chosen which retains more than 50% of the biological activity of the material, based on the activity prior to incubation, preferably at least 70%, in particular more than 85%. Retention of the biological activity means that the proteins contained in the biological material can fulfill their naturally ascribed function or the different functions, respectively. This biological activity may then be determined and stated depending on the type of protein, e.g. by means of a standardized chromogenic assay or by antigen determination. Optionally, the chemical agent is removed after incubation.

By detergent, quite general a synthetic, organic, surface-active substance is to be understood.

Preferably, a non-ionic detergent is used in the method according to the invention. Non-ionic tensides, such as polyether, in particular alkyl phenol polyglykol ether, are i.a. products of ethoxylation of fatty acids, fatty acid amides, fatty amines, fatty alcohols, aminoxides, fatty acid esters of polyalcohols and sugar esters.

Such a tenside does not have a denaturing action on the proteins and preferably is selected from the group of polysorbate and Triton. As the polysorbate, e.g., Tween® is used.

If detergents are used as the chemical agents, according to a preferred embodiment the former are used without addition of other agents, in particular without the addition of toxic organic substances or solvents, such as, e.g., TNBP In this manner, a risk or contamination is reduced to a minimum.

According to the method of the invention, the biological material is incubated with a chemical agent. Incubation means contacting the biological material with a solution, suspension or emulsion of a chemical agent for a period of time sufficiently long to inactivate possibly present pathogens or pyrogens, at a certain temperature. Contacting may, e.g., be effected by simply allowing the mixture to stand for a defined period of time.

Incubation is effected according to the present invention in the presence of an eluotropic salt. By "eluotropic salt" in the following the salt in mixture with chemical agents or the salt in a complex composition is to be understood with the property of dissolving adsorbed substances out of solid or liquid-impregnated, also gel-type adsorbents and/or of displacing them. Preferably, the eluotropic salt is a desorption agent, as is employed in chromatographic methods. The adsorbed substance is i.a. sufficiently soluble in the presence of the eluotropic salt, i.e. preferably conditions are chosen which do not precipitate the biological material.

The type and concentration of the salt or of the composition, respectively, is generally chosen in dependence on the adsorbent used. The eluting action of the salt, e.g., depends on the polarity of the solvent, i.e. it increases e.g. in the sequence ethanol—acetone—methanol—water. The adsorbent can be a solid phase, in particular a matrix suitable for ion exchange chromatography. In the composition containing the eluotropic salt also further additives may be contained, e.g. further salts. Preferably, the composition is an aqueous composition hating a pH in the range between 6.0 to 8.0, preferably around 7.0.

In a preferred embodiment, sodium chloride is used as the eluotropic salt, yet also other alkaline or alkaline earth salts, among them $CaCl_2$, are used. As the eluotropic salts, also so-called chaotropic agents, such as, e.g., urea, rhodanides or guanidinium can be employed. The concentration of the salt is at least $\geq 200$ mmol/l, preferably $\geq 300$ mmol/l. The upper limit for the concentration used will particularly depend on the solubility of the respective salt and for NaCl, e.g., it is around 2 mol/l. Chaotropic substances, such as, e.g., urea, may optionally be used even up to a concentration of 8 mol/l.

Incubation of the biological material with the chemical agent is effected for a period of time sufficiently long to inactivate any pathogens possibly present, preferably for a period of time of between 10 min and 10 h, most preferred between 1 h and 5 h. The time required for the method according to the invention can be determined by means of model viruses, such as HIV, Sindbis, TBE or hepatitis viruses in a pre-assay.

Also the choice of temperature influences the period of time to be used. In the method according to the invention, incubation is preferably effected at room temperature, e.g. in a temperature range of between 15 and 45° C., in particular between 20 and 30° C.

In the method according to the invention, the biological material preferably is adsorbed on a solid carrier, purified, and incubation is carried out immediately after elution of the purified material. Elution and incubation may be carried out consecutively, they may, however, also occur simultaneously.

According to a further preferred embodiment, incubation is carried out after a chromatographic purification of a biological material, the eluate having been further processed, e.g. by centrifugation, filtration or other physical methods.

The solid carrier preferably is a material suitable for chromatography, in particular a material suitable for ion exchange chromatography, hydrophobic chromatography or affinity chromatography. Materials such as Sepharose®, Superdex®, Sephadex®, Spherodex®, Toyopearl®, or inorganic materials, such as hydroxyl apatite, are, e.g., used.

As the ion exchanger, anion exchange materials, such as, e.g., DEAE-Sephacel®, DEAE-Sephadex®, DEAE-Sepharose® CL6B DEAE-Sepharose®Fast Flow, QAE-Sephadex®, Q-Sepharose®Fast Flow, Q-Sepharose® High Performance, DEAE-Tris-acryl, DEAE-Spherodex®, Q-Hyper-D (obtainable through Sepracor), DEAE-Toyopearl®, QAE-Toyopearl®, Fractogel® EMD-TMAE or other Fractogel materials can be used.

As examples of hydrophobic chromatographic materials, e.g. butyl-Sepharose®, octyl-Sepharose®, phenyl-Sepharose®, Fractogel®TSK-butyl, t-butyl-HIC Support or TSK Gel Butyl Toyopearl® should be mentioned.

The biological material may be adsorbed directly on the carrier from a complex mixture and purified, the inactivation step, may, however, also be preceded or followed by further steps for purifying the material, further chromatographic purification steps being preferred within the scope of the present invention.

By the method according to the invention, pathogens are inactivated. By pathogen, also fragments of, e.g., viruses, in particular also the isolated genome or its fragments, are understood.

The pathogens may be lipid-enveloped pathogens, such as, e.g., hepatitis B; virus, or non-lipid-enveloped pathogens, such as, e.g., hepatitis A virus.

At present, virus inactivation methods are called effective, if after using the method on a sample of a biological material which had been admixed with a high dose of a test virus, e.g. HI virus or Sindbis virus as a model virus for hepatitis viruses, viruses cannot be detected any longer in the sample, the virus titer thus having been reduced to below the detection limit. Detection and quantitation of nucleic acids may, e.g., be effected by means of a PCR method as described in AT patent 401,062, or by direct titration.

As a measure of inactivation, the so-called reduction factor is known which, after a single addition of test virus, is calculated from the decadic logarithm of the quotient of starting and final virus titers. From the European Guideline EC III/8115/89-EN of the Commission of the European Communities, furthermore the so-called total reduction factor is known. It is calculated from the sum of the reduction factors of individual, subsequent inactivation methods.

Also a further, independent step for inactivating or depleting, respectively, pathogens is preferably carried out. For this, all the methods known from the prior art can be used, to minimize the risk of infection.

In particular, a filtration and/or a heat treatment is effected as a further inactivation or depletion step.

As the filtration, preferably a nanofiltration is performed. A preferred heat treatment is carried out on solid biological material, e.g. on a lyophilisate having a controlled water content, e.g. a water content of between 5 to 8%, and at a temperature of between 50 and 80° C., as described in EP-0 159 311.

In a preferred embodiment, a 2-step treatment with a detergent as the chemical agent is provided. Therein, a detergent in an amount of at least 1%, preferably at least 5%, most preferred at least 10%, is used in a first step. In a second step, a further detergent is used in an amount of at least 10%, preferably at least 12%, most preferred at least 14%. The detergent used may be the same one for both steps, however, also different detergents may be used. Quite generally, the risk of a virus infection after administration of a corresponding preparation can be highly reduced or excluded by the combination of steps for virus inactivation.

According to the present invention, also a chromatographically purified preparation is provided, comprising an autodynamically activatable blood factor having a portion of activated blood factor of less than 50%, based on the content of activated and non-activated blood factor, preferably less than 40%, more preferred less than 30%, even more preferred less than 20%, further preferred less than 10%, most preferred less than 1%, and a detergent content.

In particular, the preparation is a prothrombin complex-containing preparation comprising a factor VIIa activity of less than 50%, based on the content of activated and non-activated factor VII, preferably less than 10%, most preferred less than 1%. The detergent content of the preparation according to the invention is in a pharmaceutically acceptable amount, preferably between 1% and the detection limit of the detergent.

By "autodynamically activatable blood factor" according to the present invention a blood factor is to be understood which is autocatalytically activatable, by surface contact or by processes, such as, e.g., chromatographic processes. In particular, such a blood factor is a factor selected from the group of factor VII, factor XII, factor XI and pre-Kallikrein.

In a Further preferred embodiment, the preparation is free from serine protease inhibitors, such as, e.g., thrombin inhibitors, and their cofactors, such as, e.g., heparin. In a special embodiment, the freedom from such substances is already given during a chromatographic process.

Therefore, the present invention also relates to corresponding preparations, obtainable by the method according to the invention.

In the preparation according to the invention, also further additives may be contained, e.g. stabilizing substances, such as amino acids.

The following examples shall explain the present invention in more detail without, however, restricting it thereto.

EXAMPLE 1

Determination of Factor VIII

The determination of factor VIII antigen in FEIBA was carried out according to the method of Moritz B. et. al. (Thromb. Haemost. 1997, Suppl:31). In this determination, factor VIII is selectively detected besides other plasma proteins in FEIBA by a monoclonal antibody directed against the light chain of the factor VIII molecule as capture antibody and by means of a monoclonal antibody also directed against the light chain of the factor VIII molecule, yet against a different epitope, as detecting antibody.

EXAMPLE 2

Determination of Phospholipid

Organically bound phopshate is extracted from the lyophilized powder of the FEIBA fraction according to the method of Folch J. et al. (J. Biol Chem. 1957, 226:497–509) by means of a solvent mixture consisting of chloroform, methanol at a ratio of 2 volume parts of chloroform to 1 volume part methanol. The extract containing the entire phospholipid portion subsequently was transferred into teflon vessels, and the organic solvents were evaporated under the flow of nitrogen. After addition of a buffer (20 mM Tris HCl, 150 mM NaCl, pH 7.4) and Oxisolv reagent (from Merck), the teflon vessels were tightly sealed and digested at 160° for 5 h. The phosphate liberated by the digestion process was quantitatively photometrically detected as a molybdate complex according to the method of Ames B. N. (Methods in Enzymology 1966, 8:115–118).

EXAMPLE 3

Preparation of a Factor VIII-binding Affinity Carrier

A CHO cell clone which produces recombinant von Willebrand factor is prepared as described in FEBS Lett. 1994; 351:345–348. By transfection with a vector encoding the cDNA of human furin (van den Ouweland et al., Nucleic Acids Res. 1990; 18:664), the cell line was made to coexpress human turin. Such stable Cell clones were fermented on a large scale on microcarriers in perfusion reactors (Bl üml et al., in: Spier R E, Griffith J B, Berthold W, eds. Animal cell technology. Oxford, London: Butterworth-Heinemann 1994:267–269).

Purification was effected as a 2-step chromatographic method according to Thromb.Haemost. 1995; 73:1160. The fraction desorbed by elution with saline was recovered and re-buffered by gel filtration over Sephadex® G25 (from Pharmacia) into a buffer containing 20 mM Tris-HCl, 150 mM NaCl, pH 7.5. Subsequently, the preparation was concentrated to a protein concentration of 3 mg/ml by ultraconcentration via an Amicon YM30 membrane (cut-off: 30,000 D). The von Willebrand factor concentration of this preparation amounted to 60 U of vWF-antigen/mg of protein.

The preparation of the recombinant von Willebrand factor was diluted to 1.5 mg/ml with a buffer containing 20 mM Tris-HCl, 150 mM NaCl, pH 7,5. A pre-activated gel suitable for affinity chromatography (Actigel, ALD-Superflow, from Sterogene) was excessively pre-washed with a buffer containing 20 mM Tris-HCl, 150 mM NaCl, pH 7.5. One volume part of the pre-washed gel was admixed with 1.1 volume parts of the protein solution to be immobilized, and subsequently 0.15 volume parts of a solution of 0.1 M cyanoborohydride ($NaCNBH_3$) in 0.1 M phosphate buffer, pH 7.0, were added. The gel was suspended in this buffer by shaking and was incubated at room temperature for 16 hours under continued shaking. Subsequently, the gel was washed on a sintered suction filter with the 10-fold volume of a buffer containing 20 mM Tris-HCl, 150 mM NaCl, pH 7.5, and with the 5-fold volume of a buffer containing 20 mM Tris-HCl, 2 M NaCl, pH 7.5. Then it was equilibrated again with 5 volume parts of the buffer, 20 mM Tris-HCl, 150 mM NaCl, pH 7.5, and the gel was transferred into a chromatographic column of a dimension diameter to gel bed height of 1:4. By determining the protein concentration in the solutions of the incubation supernatant of the von Willebrand factor solution and the affinity gel as well as of the washing solutions separated on the sintered suction filter, a coupling rate of more than 90% of the protein employed could be determined.

EXAMPLE 4

Preparation of a Factor VIII-free Prothrombin Complex by Contact with an Affinity Gel (at present considered by Applicant to be the best mode of carrying out the invention)

The pharmaceutical preparation FEIBA S-TIM4 IMMUNO (1000 units) was reconstituted with 20 ml of distilled water. Upon complete dissolution of the freeze-dried powder, the solution contained an active substance concentration of 50 units per ml. 10 ml of this solution were contacted with 100 mg of the previously described immobilized von Willebrand factor and incubated for 1 h with gentle shaking at room temperature. Subsequently, the immobilisate was removed by filtration via a sintering suction filter. The FEIBA solution contained in the filtrate had an activity of 49 units of FEIBA/ml. By binding the factor VIII contained in the preparation to immobilized von Willebrand factor, factor VIII antigen in this preparation was below the detection limit.

EXAMPLE 5

Preparation of Factor VIII-free Activated Prothrombin Complex by Readsorption on a Non-specific Carrier 15 mg of DEAE-Sephadex® A-50 from Pharmacia were incubated for 15 min at room temperature with 1 ml of a solution of 30 g/l NaCl in water until swelling. Then the gel was separated from the swelling supernatant by centrifugation. There followed five washings of the gel with 1 ml of buffer each (9 g/l $Na_2HPO_4.2H_2O$, 7 g/l NaCl, pH 7.0), and further two washings with a buffer (7 g/l $Na_3$ citrate.$2H_2O$, 7 g/l NaCl) also by resuspending and centrifuging.

30 ml of fresh frozen human citrated plasma were thawed at 0–+4° C., and the cryoprecipicate incurred was separated by centrifuging at +2° C. The "cryo-supernatant" resulting therefrom was incubated with the washed DEAE-Sephadex®, FEIBA being generated and adsorbed on the gel together with the factors of the prothrombin complex, factor VIII and inert protein. Thereafter, coadsorbed inert protein was removed from the DEAE gel by washing with a buffer (9 g/l $Na_2HPO_4.2H_2O$, 7 g/l NaCl).

The buffer-moist gel protein complex was now suspended with 1.5 ml of a solution of 150 mg/ml TWEEN®–80 and 30 mg/ml NaCl for 1 h at 26° C. By the treatment with the solution of high ionic strength, protein was desorbed together with the factors of the prothrombin complex and factor VIII. Subsequently, the suspension was diluted by adding 6.5 ml of water and readsorbed for 1 h at room temperature, the prothrombin complex fraction again being readsorbed. Simultaneously, only a small portion of the factor VIII contained in the protein fraction was readsorbed on the gel. The gel/protein complex was then washed five times detergent-free with 1 ml each of a solution of 7 g/l NaCl in water.

For elution, the gel was treated with 0.7 ml of a solution of 30 g/l NaCl in water with stirring. The eluate was now dialysed against distilled water, frozen, and lyophilized. After reconstitution of the lyophilisate, the FEIB activity was determined according to AT 350,726.

Furthermore, the factor VIII antigen content was determined. As the control, a conventionally produced FEIBA preparation as it is described in AT 350,726 was used. The preparation recovered according to the described method had a factor VIII content reduced by a factor 10 as compared to the control.

Due to the contact with the detergent, also pathogens possibly present, in particular lipid-enveloped viruses, were inactivated.

EXAMPLE 6
Preparation of Factor VIII-free and Phospholipid-free Activated Prothrombin Complex by Readsorption on a Non-specific Carrier 15 mg of DEAE-Sephadex® A-50, from Pharmacia, were incubated until swelling at room temperature with 1 ml of a solution of 30 g/l NaCl in water for 15 minutes. Then the gel was separated from the swelling supernatant by centrifugation. This was followed by five washings of the gel with 1 ml of buffer each (9 g/l $Na_2HPO_4.2H_2O$, 7 g/l NaCl, pH 7.0), and two further washings with a buffer (7 g/l $Na_3$ citrate.$2H_3O$, 7 g/l NaCl), also by resuspension and centrifuging.

30 ml of fresh frozen human citrated plasma were thawed at 0–+4° C., and the cryoprecipitate incurred was separated by centrifugation at +2° C. The "cryosupernatant" resulting therefrom was incubated with the washed DEAE-Sephadex®, FEIBA being generated and adsorbed on the gel together with the factors of the prothrombin complex, factor VIII, phospholipid and inert protein. Subsequently, coadsorbed inert protein was removed from the DEAE gel by washing with a buffer (9 g/l $Na_2HPO_4.2H_2O$, 7 g/l NaCl).

The buffer-moist gel protein complex now was suspended with 1.5 ml of a solution of 1 mg/ml TWEEN®–80 and 30 mg/ml NaCl for 1 h at room temperature, the protein fraction and non-specifically adsorbed impurities being desorbed. Subsequently, the gel was separated by filtration. The protein solution now was brought to a detergent concentration of 150 mg/ml by further addition of TWEEN®–80, and subsequently it was incubated with stirring at 40° C. for 1 h. Subsequently, it was diluted by adding 6.5 ml of water, and a fresh washed prepared DEAE-Sephadex® A-50 gel was readsorbed, the prothrombin complex fraction again being readsorbed. Simultaneously, only a small portion of the factor VIII contained in the protein fraction was bound to the gel. Subsequently, it was washed detergent-free by five washings with 1 ml each of a solution of 7 g/l NaCl in water. In doing so, also bound phospholipid, which was present in solubilized state due to the contact with the amphiphilic agent, was removed.

For elution, the gel was treated with 0.7 ml of a solution of 30 g/l NaCl in water with stirring. The eluate now was dialyzed against distilled water, frozen, and lyophilized. After reconstitution of the lyophilisate, the FEIB activity was determined according to AT-B 350 726.

Moreover, the factor VIII antigen content and phospholipid were determined as described. As the control, a conventionally produced FEIBA preparation was used, which was recovered according to AT 350,726. The preparation obtained according to the method described has a F VIII content reduced as compared to the control and was free from phospolipid. The results of the analyses are summarized in Table 1.

TABLE 1

FEIBA:FVIII/Phospholipid Content

| | FEIBA U/ml | FVIIIC:Ag U/ml | FVIIIC:Ag FEIBA U/U | Phospholipid nM Phosphate/ U FEIBA |
|---|---|---|---|---|
| FEIBA (Standard) | 51 | 7.0 | 0.14 | 0.14 |
| FEIBA (Product of invention) | 70 | 1.0 | 0.01 | <0.02 |

What is claimed is:

1. An immunotolerant pharmaceutical prothrombin complex preparation comprising factors II, IX, and X, and comprising a factor VIII antigen content of less than 0.1 factor VIII:C antigen/U FEIBA, wherein said immunotolerant pharmaceutical prothrombin complex preparation does not include fibrinogen and heparin.

2. A pharmaceutical preparation as set forth in claim 1, further comprising factor VII.

3. A pharmaceutical preparation as set forth in claim 1, said preparation being produced from plasma or a plasma fraction.

4. A pharmaceutical preparation as set forth in claim 2, said preparation being produced from plasma or a plasma fraction.

5. A pharmaceutical preparation as set forth in claim 1, further comprising at least one of factors IXa, Xa and VIIa and having FEIB activity.

6. A pharmaceutical preparation as set forth in claim 2, further comprising at least one of factors IXa, Xa and VIIa and having FEIB activity.

7. A pharmaceutical preparation as set forth in claim 1, said preparation being free from phospholipids.

8. A pharmaceutical preparation as set forth in claim 2, said preparation being free from phospholipids.

9. A method for producing an immunotolerant pharmaceutical prothrombin complex preparation comprising factors II, IX, and X, and having a factor VIII antigen content of less than 0.1 factor VIII:C antigen/U FEIBA, wherein said immunotolerant pharmaceutical prothrombin complex preparation does not include fibrinogen and heparin, said method comprising the steps of:
   (a) providing a plasma or plasma fraction comprising factors II, IX, and X,
   (b) contacting said plasma or said plasma fraction with a carrier material so as to separate factor VIII from factors II, IX, and X,
   (c) purifying said plasma or plasma fraction, and
   (d) recovering a fraction comprising factors II, IX, and X.

10. A method as set forth in claim 9, wherein said contacting of said plasma or said plasma fraction with said carrier material is effected in the presence of a detergent.

11. A method as set forth in claim 9, wherein phospholipids are also separated when factor VIII is separated from said factors II, IX and X.

12. A method for producing an immunotolerant pharmaceutical prothrombin complex preparation comprising factors II, IX, X and VII, and having a factor VIII antigen content of less than 0.1 factor VIII:C antigen/U FEIBA, wherein said immunotolerant pharmaceutical prothrombin complex preparation does not include fibrinogen and heparin, said method comprising the steps of:
   (a) providing a plasma or plasma fraction comprising factors II, IX, X and VII,
   (b) contacting said plasma or said plasma fraction with a carrier material so as to separate factor VIII from factors II, IX, X and VII, (c) purifying said plasma or plasma fraction, and
(d) recovering a fraction comprising factors II, IX, X and VII.

13. A method as set forth in claim 12, wherein said contacting of said plasma or said plasma fraction with said carrier material is effected in the presence of a detergent.

14. A method as set forth in claim 12, wherein phospholipids are also separated when factor VIII is separated from said factors II, IX, X and VII.

15. A method as set forth in claim 9, wherein steps (b) and (c) are carried out in one method step.

16. A method as set forth in claim 12, wherein steps (b) and (c) are carried out in one method step.

17. A method as set forth in claim 9, wherein said carrier material is a material suitable for at least one of chromatography, filtration and nanofiltration.

18. A method as set forth in claim 12, wherein said carrier material is a material suitable for at least one of chromatography, filtration and nanofiltration.

19. A method as set forth in claim 12, wherein said carrier material is a factor VIII specific carrier material.

20. A method as set forth in claim 12, wherein said carrier material is a factor VIII specific carrier material.

21. A method as set forth in claim 19, wherein said factor VIII specific carrier material is a matrix suitable for affinity chromatography.

22. A method as set forth in claim 20, wherein said factor VIII specific carrier material is a matrix suitable for affinity chromatography.

23. A method as set forth in claim 21, wherein said matrix is a vWF-containing matrix.

24. A method as set forth in claim 22, wherein said matrix is a vWF-containing matrix.

25. A method as set forth in claim 9, wherein said factor VIII is adsorbed on said carrier material.

26. A method as set forth in claim 11, wherein said factor VIII and said phospholipids are adsorbed on said carrier material.

27. A method as set forth in claim 12, wherein said factor VIII is adsorbed on said carrier material.

28. A method as set forth in claim 14, wherein said factor VIII and said phospholipids are adsorbed on said carrier material.

29. A method as set forth in claim 9, wherein said carrier material has a higher affinity for the prothrombin complex than for factor VIII.

30. A method as set forth in claim 12, wherein said carrier material has a higher affinity for the prothrombin complex than for factor VIII.

31. A method as set forth in claim 29, wherein said carrier material is a weak anion exchanger.

32. A method as set forth in claim 30, wherein said carrier material is a weak anion exchanger.

33. A method as set forth in claim 29, wherein factors II, IX and X are adsorbed on said carrier material, while factor VIII is eluted.

34. A method as set forth in claim 30, wherein factors II, IX, X and VIII are adsorbed on said carrier material, while factor VIII is eluted.

35. A method as set forth in claim 33, wherein said phospholipids are also separated when factor VIII is separated from said factors II, IX and X, said phospholipids being eluted together with factor VIII.

36. A method as set forth in claim 34, wherein said phospholipids are also separated when factor VIII is separated from said factors II, IX, X and VII, said phospholipids being eluted together with factor VIII.

37. A method as set forth in claim 29, wherein factors II, IX and X are not bound to the carrier material.

38. A method as set forth in claim 30, wherein factors II, IX, X and VII are not bound to the carrier material.

39. A method as set forth in claim 10, wherein said detergent is a non-ionic detergent.

40. A method as set forth in claim 13, wherein said detergent is a non-ionic detergent.

41. A method as set forth in claim 39, wherein said non-ionic detergent is a polyether.

42. A method as set forth in claim 40, wherein said non-ionic detergent is a polyether.

43. A method as set forth in claim 10, further comprising removing said detergent after contact with said plasma or said plasma fraction.

44. A method as set forth in claim 13, further comprising removing said detergent after contact with said plasma or said plasma fraction.

45. A method as set forth in claim 9, wherein said plasma fraction is selected from the group consisting of a product of chromatography, a product of precipitation, a product of centrifugation and a cryoprecipitate supernatant.

46. A method as set forth in claim 12, wherein said plasma fraction is selected from the group consisting of a product of chromatography, a product of precipitation, a product of centrifugation and a cryoprecipitate supernatant.

47. A method as set forth in claim 9, wherein said plasma fraction has at least an intermediary purity.

48. A method as set forth in claim 12, wherein said plasma fraction has at least an intermediary purity.

49. A method as set forth in claim 9, further comprising at least one step for inactivating or depleting viruses or virus components.

50. A method as set forth in claim 12, further comprising at least one step for inactivating or depleting viruses or virus components.

51. A method as set forth in claim 49, wherein said at least one step for inactivating or depleting viruses or virus components is selected from the group consisting of a heat treatment, a vapor treatment, a treatment with a solvent and a treatment with a detergent and nanofiltration.

52. A method as set forth in claim 50, wherein said at least one step for inactivating or depleting viruses or virus components is selected from the group consisting of a heat treatment, a vapor treatment, a treatment with a solvent and a treatment with a detergent and nanofiltration.

53. A preparation as set forth in claim 1, obtainable by
(a) providing a plasma or a plasma fraction comprising factors II, IX and X,
(b) contacting said plasma or said plasma fraction with a carrier material so as to separate factor VIII from factors II, IX and X,
(c) purifying said plasma or plasma fraction, and
(d) recovering a fraction comprising factors II, IX and X.

54. A preparation as set forth in claim 1, obtainable by
(a) providing a plasma or a plasma fraction comprising factors II, IX, X and VII,
(b) contacting said plasma or said plasma fraction with a carrier material so as to separate factor VIII from factors II, IX, X and VII,
(c) purifying said plasma or plasma fraction, and
(d) recovering a fraction comprising factors II, IX, X and VII.

55. A method for treating hemophilia A patients, said method comprising administering to said patients an effective amount of an immunotolerant pharmaceutical prothrombin complex preparation comprising factors II, IX and X, and having a factor VIII antigen content of less than 0.1 factor VIII:C antigen/U FEIBA.

56. A method for treating hemophilia A patients, said method comprising administering to said patients an effective amount of an immunotolerant pharmaceutical prothrombin complex preparation comprising factors II, IX, X and VII, and having a factor VIII antigen content of less than 0.1 factor VIII:C antigen/U FEIBA.

57. A method as set forth in claim 55, wherein said patients have an inhibitor titer of greater than 1 Bethesda U/ml plasma.

58. A method as set forth in claim 56, wherein said patients have an inhibitor titer of greater than 1 Bethesda U/ml plasma.

59. A method as set forth in claim 55, wherein said patients have an inhibitor titer of greater than 5 Bethesda U/ml plasma.

60. A method as set forth in claim 56, wherein said patients have an inhibitor titer of greater than 5 Bethesda U/ml plasma.

* * * * *